(12) United States Patent
Lovell

(10) Patent No.: US 9,962,175 B2
(45) Date of Patent: May 8, 2018

(54) METHODS OF USE OF AN ANATOMIC STRUCTURE EXTRACTOR

(71) Applicant: Gary Lovell, Rexburg, ID (US)

(72) Inventor: Gary Lovell, Rexburg, ID (US)

(*) Notice: Subject to any disclaimer, the term of this patent is extended or adjusted under 35 U.S.C. 154(b) by 34 days.

(21) Appl. No.: 14/943,241

(22) Filed: Nov. 17, 2015

(65) Prior Publication Data

US 2016/0066899 A1    Mar. 10, 2016

Related U.S. Application Data

(63) Continuation-in-part of application No. 14/055,754, filed on Oct. 16, 2013, now Pat. No. 9,308,357.

(51) Int. Cl.
*A61B 17/3205* (2006.01)
*A61B 17/42* (2006.01)
(Continued)

(52) U.S. Cl.
CPC .......... *A61B 17/22* (2013.01); *A61B 10/0266* (2013.01); *A61B 10/0283* (2013.01); *A61B 17/32002* (2013.01); *A61B 17/3205* (2013.01); *A61B 17/3421* (2013.01); *A61B 17/42* (2013.01); *A61B 90/30* (2016.02); *A61B 2017/00278* (2013.01); *A61B 2017/00287* (2013.01); *A61B 2017/00349* (2013.01); *A61B 2017/00818* (2013.01); *A61B 2017/00823* (2013.01); *A61B 2017/00902* (2013.01); *A61B 2017/00907* (2013.01); *A61B 2017/12018* (2013.01); *A61B 2017/22079* (2013.01); *A61B 2017/306* (2013.01); *A61B 2017/320024* (2013.01); *A61B 2017/3419* (2013.01); *A61B 2017/3445* (2013.01); *A61B 2017/3458* (2013.01); *A61B 2017/3466* (2013.01); *A61B 2017/3488* (2013.01);
(Continued)

(58) Field of Classification Search
CPC .. A61M 1/0058; A61M 1/0064; A61M 1/008; A61B 2017/308; A61B 2017/306; A61B 2017/12018; A61B 17/12009; A61F 6/208
See application file for complete search history.

(56) References Cited

U.S. PATENT DOCUMENTS 958,854 A    5/1910 Bunn
2,911,968 A    11/1959 Schueler
(Continued)

*Primary Examiner* — Adam Marcetich
(74) *Attorney, Agent, or Firm* — Schmeiser, Olsen & Watts LLP

(57) ABSTRACT

An anatomic structure extractor allows a medical practitioner to retract, aspirate, ligate and amputate an anatomic structure within a patient through a minimally invasive incision. An anatomic structure extractor may include a transparent tubular member with a cap coupled to one end. The cap may have at least one view port with a magnifying lens. The cap may also have a needle port through which a needle is inserted to puncture the anatomic structure. A trap may be in fluid communication with the transparent tubular member. A suction post is in communication with the trap to pull the contents of an aspirated cyst into the trap. A light post containing a light source may be connected to the transparent tubular member to illuminate the interior of the extractor. A ligature deployer and a cutting wire may also be coupled to the tubular member.

19 Claims, 10 Drawing Sheets

(51) Int. Cl.
  *A61B 17/32* (2006.01)
  *A61B 17/22* (2006.01)
  *A61B 17/12* (2006.01)
  *A61B 17/34* (2006.01)
  *A61B 10/02* (2006.01)
  *A61B 17/00* (2006.01)
  *A61B 90/30* (2016.01)
  *A61B 90/00* (2016.01)
  *A61B 17/30* (2006.01)

(52) U.S. Cl.
  CPC ........... *A61B 2017/4216* (2013.01); *A61B 2090/3616* (2016.02); *A61B 2217/005* (2013.01)

(56) References Cited

U.S. PATENT DOCUMENTS

| | | | |
|---|---|---|---|
| 3,592,199 A | 7/1971 | Ostensen | |
| 3,685,509 A | 8/1972 | Bentall | |
| 5,169,397 A | 12/1992 | Sakashita | |
| 5,314,406 A | 5/1994 | Arias | |
| 5,531,722 A | 7/1996 | Van Hale | |
| 5,810,806 A | 9/1998 | Ritchart | |
| 5,971,996 A * | 10/1999 | Tugendreich | A61B 17/42 128/898 |
| 6,027,502 A | 2/2000 | Desai | |
| 6,159,209 A * | 12/2000 | Hakky | A61B 17/32002 604/22 |
| 6,280,415 B1 | 8/2001 | Johnson | |
| 6,468,228 B1 * | 10/2002 | Topel | A61B 17/32053 600/564 |
| 6,558,379 B1 | 5/2003 | Batchelor | |
| 2002/0026199 A1 | 2/2002 | Fortier | |
| 2002/0072757 A1 * | 6/2002 | Ahmed | A61B 17/12013 606/139 |
| 2004/0138645 A1 * | 7/2004 | Lonky | A61B 17/00234 604/540 |
| 2004/0143169 A1 | 7/2004 | Branch | |
| 2005/0124986 A1 * | 6/2005 | Brounstein | A61B 18/00 606/39 |
| 2005/0143757 A1 | 6/2005 | Ghareeb | |
| 2005/0251162 A1 | 11/2005 | Rothe | |
| 2007/0239182 A1 * | 10/2007 | Glines | A61B 17/22012 606/159 |
| 2008/0009855 A1 * | 1/2008 | Hamou | A61B 17/32002 606/46 |
| 2008/0091061 A1 | 4/2008 | Kumar | |
| 2008/0091074 A1 | 4/2008 | Kumar | |
| 2008/0255412 A1 * | 10/2008 | Surti | A61B 17/12013 600/104 |
| 2010/0305566 A1 * | 12/2010 | Rosenblatt | A61B 17/0469 606/49 |
| 2011/0046442 A1 | 2/2011 | Matsushita | |
| 2011/0152776 A1 | 6/2011 | Hartoumbekis | |
| 2013/0023788 A1 * | 1/2013 | Gostout | A61B 10/04 600/564 |

* cited by examiner

METHODS OF USE OF AN ANATOMIC STRUCTURE EXTRACTOR

CROSS REFERENCE TO RELATED APPLICATION

This application claims priority to U.S. patent application Ser. No. 14/055,754 to Gary Lovell entitled "CYST EXTRACTOR, filed Oct. 16, 2013, the disclosure of which is hereby incorporated entirely herein by reference.

BACKGROUND OF THE INVENTION

Technical Field

This invention relates to methods of using a device for removing anatomic structures from the body, such as solid structures, cystic structures, organs such as a gallbladder or an appendix, and the like.

State of the Art

Surgeons are often required to remove or partially resect fluid or semi-fluid filled intra-abdominal and/or intrathoracic masses or organs for various accepted clinical indications. Such indications include but are not limited to treatment of infection, diagnosis from a tissue sample, treatment of cystic masses, and controlled drainage of infected, malignant, or endometriotic cystic contents without contamination or soiling of the peritoneal or thoracic cavities.

Options currently available for draining fluid, obtaining tissue, or resecting masses, however, are limited. For example, surgical procedures are commonly performed laparoscopically and involve multiple puncture incisions of the abdominal or chest wall. Multiple incisions create additional potential sites for wound infection, incisional hernia, pain, and other complications. Additionally, laparoscopic surgery requires either retraction of the abdominal wall or insufflation of gas to expand the intraperitoneal space, creating exposure for the surgeon to visualize and safely manipulate tissue. These maneuvers require general or high-spinal anesthesia for pain control, and to properly relax the abdominal wall. There is a risk of serious and potentially lethal complications associated with general and spinal anesthesia, such as myocardial infarction, stroke, malignant hyperthermia, pulmonary thromboembolism, and others.

Accordingly, methods of using a device are needed for draining and removing cystic and other masses, appendices, gallbladders, and the like, which allows the medical practitioner to easily view, manipulate, aspirate, and amputate the contents and potentially remove the structure through a single limited incision without the need for refraction and relaxation of the abdominal or chest wall and general/spinal anesthesia.

SUMMARY OF EMBODIMENTS

The anatomic structure extractor, as discloses herein below, may be used to drain, biopsy, and resect cystic and solid masses, cystic lesions, tumors, infected fluid collections, small organs such as appendices and gallbladders, and the like according to the methods described herein. Embodiments of the method include use of an anatomic structure extractor comprising a tubular member; a cap coupled to a proximal end of said tubular member, wherein said cap further comprises at least one view port and at least one needle port; a trap in fluid communication with said tubular member wherein accumulation of a material in said trap does not impede a user's view through said tubular member; a suction post in communication with said trap; and a light post coupled to said tubular member.

Disclosed is a method for using an anatomic structure extractor comprising the steps of inserting an anatomic structure extractor comprising a tubular member and a handle in fluid communication with the tubular member into a body; coupling the anatomic structure extractor to an anatomic structure; and extracting the anatomic structure coupled to the anatomic structure extractor from the body.

In some embodiments, the anatomic structure is a non-fluid-filled structure. In some embodiments, the anatomic structure is a solid structure. In some embodiments, the inserting step comprises a trans-vaginal insertion. In some embodiments, the inserting step comprises a trans-cutaneous insertion. In some embodiments, the inserting step comprises a trans-mucosal insertion.

In some embodiments, the coupling step comprises applying a vacuum to a suction post. In some embodiments, the coupling step comprises boring a corkscrew needle inserted through a needle port in the anatomic structure extractor into the anatomic structure.

Disclosed is a method for using an anatomic structure extractor comprising the steps of coupling the anatomic structure extractor to an anatomic structure; boring a morcellizing auger coupled to the anatomic structure extractor into the anatomic structure; and operating the morcellizing auger causing a material to be removed from the anatomic structure.

In some embodiments, the method further comprises a suctioning step, wherein removal of the material from the anatomic structure is facilitated by applying a vacuum to a suction post of the anatomic structure extractor. In some embodiments, the method further comprises a step of morcellizing the material comprising the anatomic structure.

Disclosed is a method for using an anatomic structure extractor comprising the steps of coupling the anatomic structure extractor to an organ in a body; and extracting the organ from the body.

In some embodiments, the method further comprises a step controlling a vascular pedicle of the anatomic structure. In some embodiments, said controlling step comprises ligating said vascular pedicle. In some embodiments, said controlling step comprises pushing a ligating band onto said vascular pedicle. In some embodiments, the organ comprises an appendix.

In some embodiments, said anatomic structure extractor comprises a tubular member; a cap coupled to an end of said tubular member wherein said cap further comprises at least one view port and at least one needle port; a trap in fluid communication with said tubular member; a suction post in communication with said trap; and a light post coupled to said tubular member. In some embodiments, said anatomic structure extractor further comprises a vacuum break in fluid communication with said suction post. In some embodiments, said anatomic structure extractor further comprises a corkscrew needle through said needle port. In some embodiments, said anatomic structure extractor further comprises a morcellizing auger inserted through said needle port. In some embodiments, said at least one view port further comprises a magnifying lens.

In some embodiments, the anatomic structure extractor further comprises suction applied to said suction post.

The foregoing and other features and advantages of the present invention will be apparent from the following more

DETAILED DESCRIPTION OF EMBODIMENTS OF THE INVENTION

Figure 1:
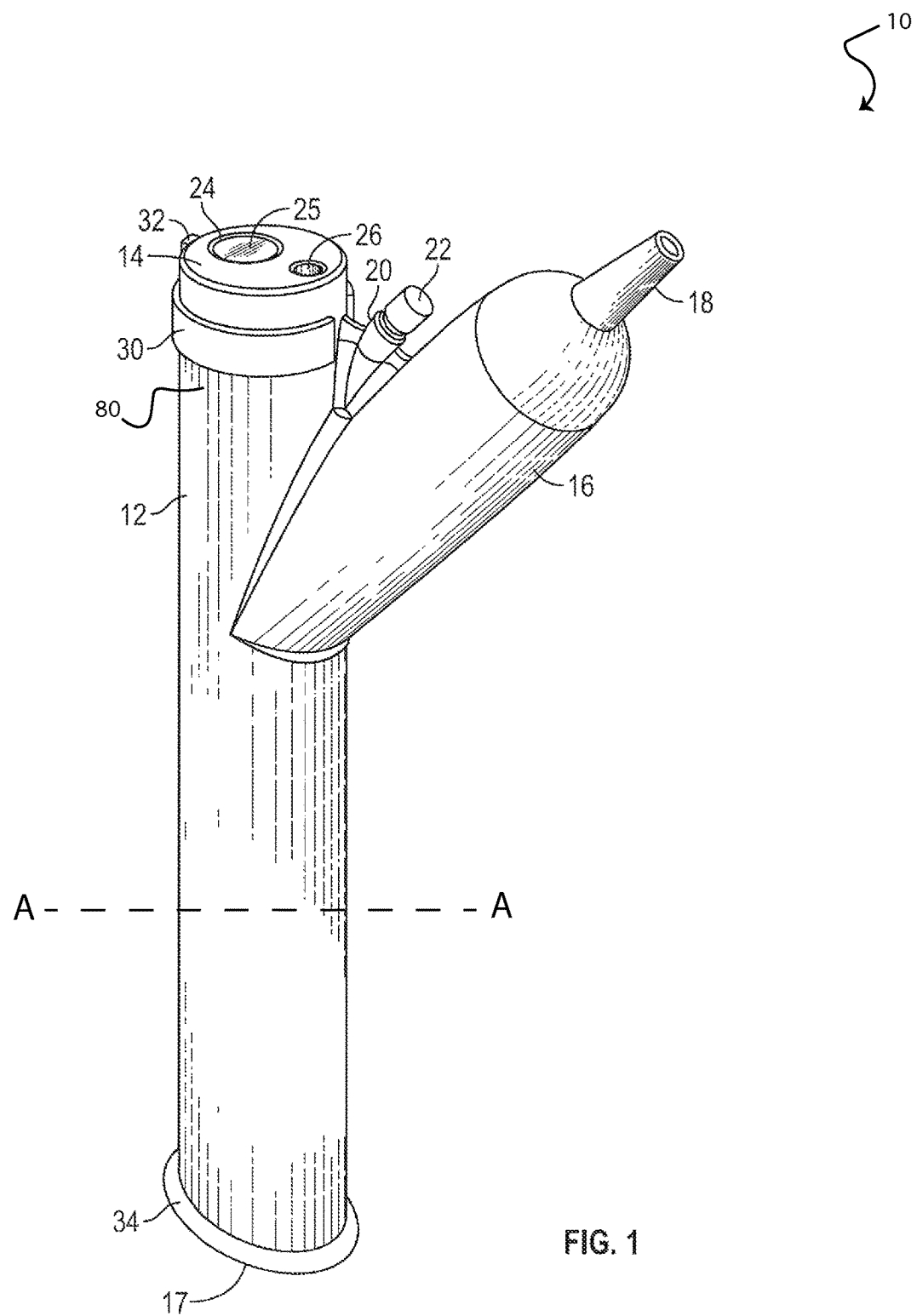
FIG. 1 is an isometric view of an anatomic structure extractor.
Figure 2:
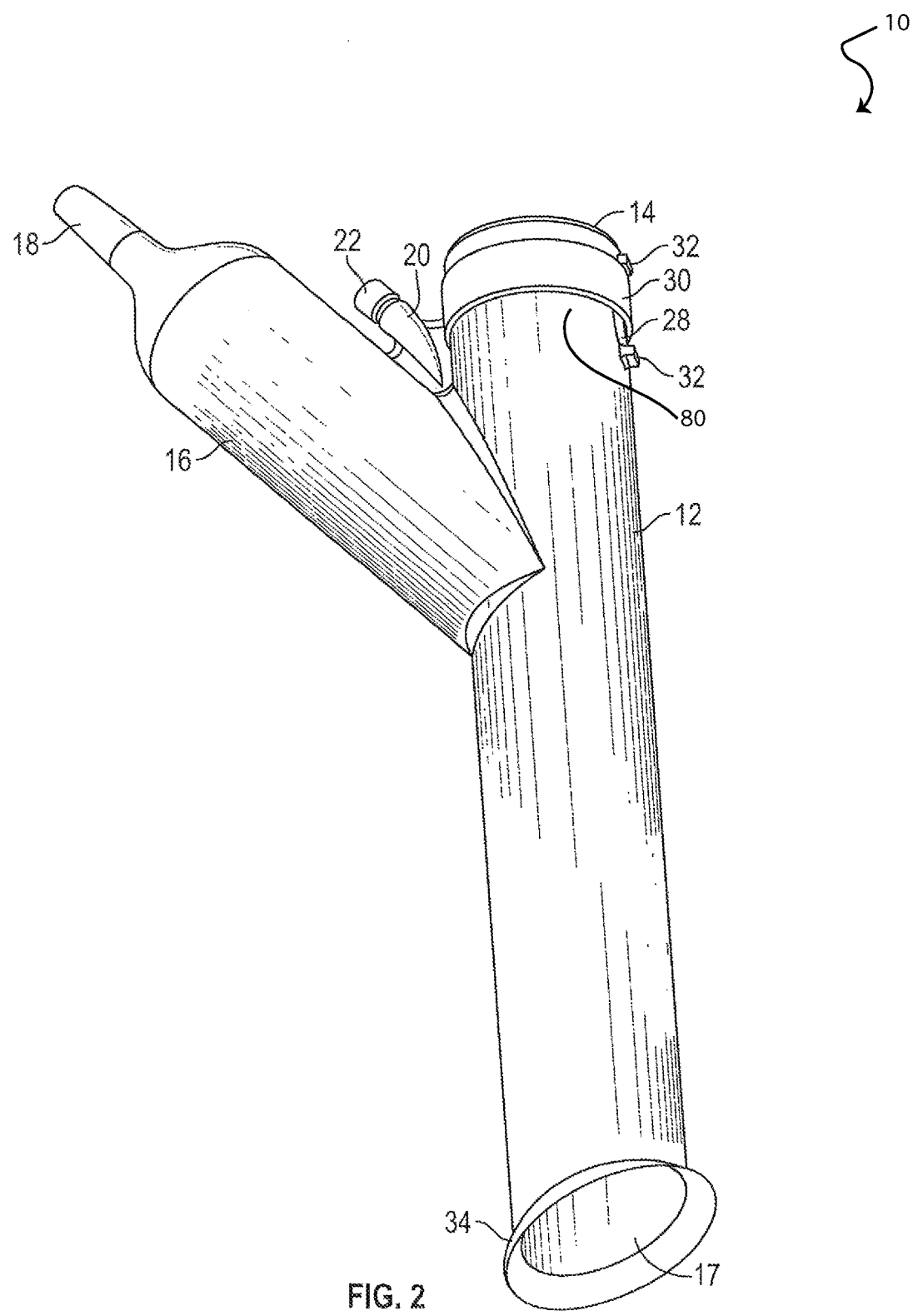
FIG. 2 is a rear isometric view of an anatomic structure extractor.

Embodiments of this invention disclose an anatomic structure extractor and method of use. For the purposes of this application, an anatomic structure is a defined tissue structure within a body, non-limiting examples including a cyst, such as an ovarian cyst; a tumor, such as a uterine fibroid; an organ, such as an appendix; and the like. As discussed herein above, a device for removing an anatomic structure from a patient may include a tubular member, a trap, a suction post, a light post, a lens, a probe, a tissue morcellizing auger, and a needle. For the purposes of this application, a cystic lesion, lesion, cystic body, or cyst may include any liquid or semi-solid organ, sack, cyst, or the like which is surrounded by a membrane, pseudomembrane, or layer of tissue and contained within a patient's body. Examples of cystic lesion, lesions, cystic bodies, or cysts according to this definition include but are not limited to pelvic cysts and abscesses of the ovary, fallopian tube, appendix, uterus; fluid collections within the gallbladder, perinephric abscesses, diverticular abscesses, retroperitoneal abscesses, necrotic tumors, pancreatic pseudocysts, lung abscesses, mediastinal abscesses and fluid collections, empyema, inflected pleural effusions, and the like. Additionally "mass" may include (but is not limited to) solid organ tumors, including nodules of the peritoneum and of structures covered by the visceral peritoneum; extraperitoneal masses including retroperitoneal masses and extraperitoneal masses of the pelvis; mediastinal masses, and masses of the lung, pleural, and extrapleural chest wall.

FIGS. 1-6 illustrate an embodiment of an anatomic structure extractor 10. Anatomic structure extractor 10, in some embodiments, includes a tubular member 12. Tubular member 12, in some embodiments, is a cannula-like device comprising a hollow cylindrical tube in the range of from about thirty (30) to about fifty (50) centimeters in length and in the range of from about 1.5 to about 4 centimeters in diameter. In some embodiments, tubular member 12 is translucent or transparent. Wherein tubular member 12 is transparent, a medical practitioner may visualize tissue or other contents contained within a lumen 82 of tubular member 12 to evaluate the extent to which an anatomical structure of interest has been withdrawn from the body. In some embodiments wherein anatomic structure extractor 10 is disposable, tubular member 12 is formed from a material which is inexpensive, such as polyethylene, polypropylene, or other synthetic plastic material, for example. In some embodiments wherein tubular member 12 is disposable, tubular member 12 is removeably coupled to a light post 20 and a cap 14. In some embodiments, cap 14 is coupled to light post 20 and removeably coupled to tubular member 12 by a threaded member, a notched member, or similar reversible solid coupling means.

Tubular member 12, as shown in FIGS. 1-4 and FIGS. 7-9 has a generally cylindrical shape with a circular or elliptical transverse cross section "A," as shown in FIG. 1. This is not, however, meant to be limiting. Tubular member 12 may be formed in any shape desired, including rectangular, square, triangular, polygonal, and the like. Tubular member 12 is also formed from any suitable commercially available material known in the medical device arts, provided the material is sufficiently strong to withstand a vacuum within lumen 82 (not shown in FIG. 1; see FIG. 3). Tubular member 12 may also be any suitable diameter and length.

Tubular member 12 further comprises a proximal end 80, as shown in FIG. 1. Proximal end 80 is coupled to cap 14. Cap 14 seals proximal end 80 of tubular member 12. Cap 14 is any size or shape which matches, or is slightly smaller or slightly larger than the size and shape of end 80 of tubular member 12. Cap 14 may be removably coupled to tubular member 12; alternatively, cap 14 may be formed as an element of tubular member 12, such as a unitary body with tubular member 12 in some embodiments. In some embodiments, the coupling between cap 14 and tubular member 12 is airtight.

FIG. 1 additionally shows cap 14 further comprising a view port 24, in some embodiments. View port 24 is an opening in cap 14 through which, in some embodiments, the medical provider may view the cyst, mass, or other anatomical structure of interests under direct vision as the procedure is performed using anatomic structure extractor 10. An "anatomical structure of interest" includes a cyst, an ovary, an appendix, a gallbladder, a tumor, a mass, an organ, a tissue, a foreign body, a solid-tissue structure, a hollow-tissue structure, and/or a fluid or semi-fluid-filled tissue structure. View port 24 may be formed in any suitable shape and size; i.e. a square, oval, rectangular, triangular, or circular shape, or the like. View port 24 is any desired size, provided it is large enough to comfortably visualize the anatomical object of interest at an open end 17, as shown in FIG. 1, through tubular member 12.

View port 24, in some embodiments, further comprises a lens 25, as shown in FIG. 1 and FIGS. 3-9. In some embodiments, lens 25 is a magnifying lens. In some such embodiments, lens 25 may magnify the anatomical structure of interest to any degree desirable to best allow the medical provider to view the structure of interest at open end 17 and safely perform any procedures, such as aspiration, biopsy, or extraction, thereon. In some embodiments, cap 14 comprises a plurality of viewports 24 and a plurality of lenses 25. In some embodiments, lens 25 is interchangeable with other lens(es) 25 such that a medical practitioner may select and switch between different magnifications. In some embodiments, lens 25 is a non-magnifying transparent cover for view port 24.

Figure 7:
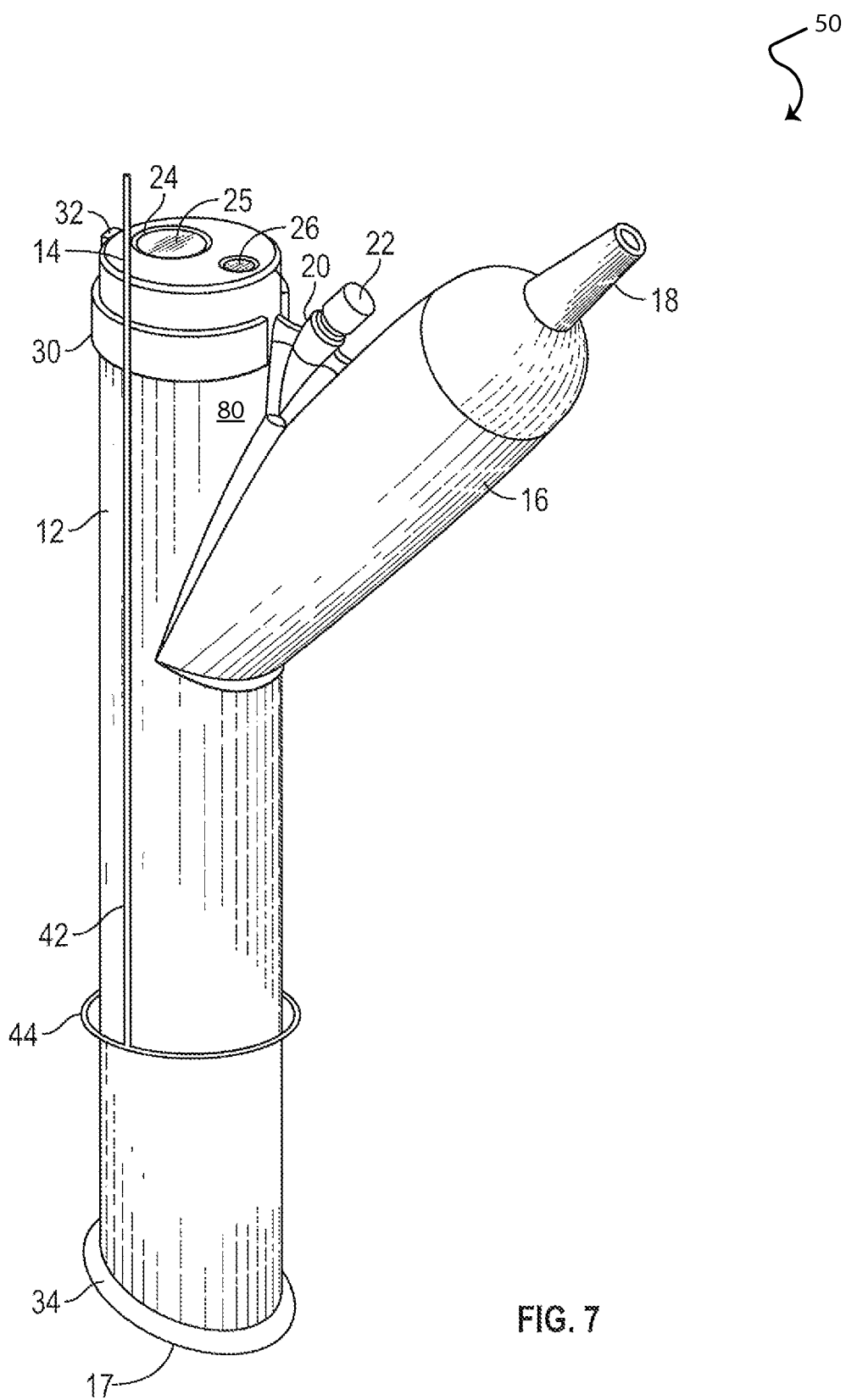
FIG. 7 is a view of an anatomic structure extractor with a cutting wire.
Figure 8:
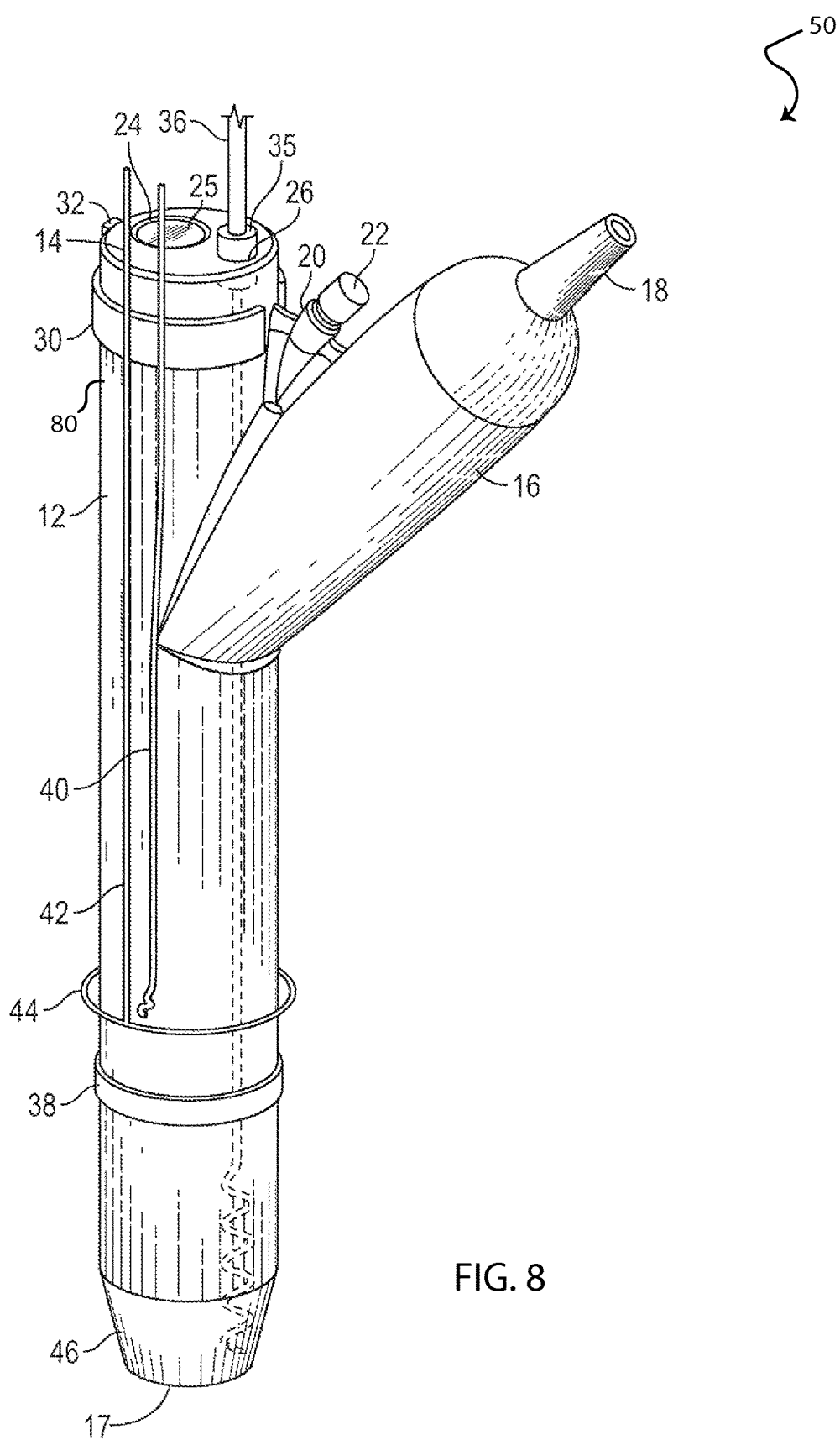
FIG. 8 is a view of an anatomic structure extractor with a ligature deployer.
Figure 9:
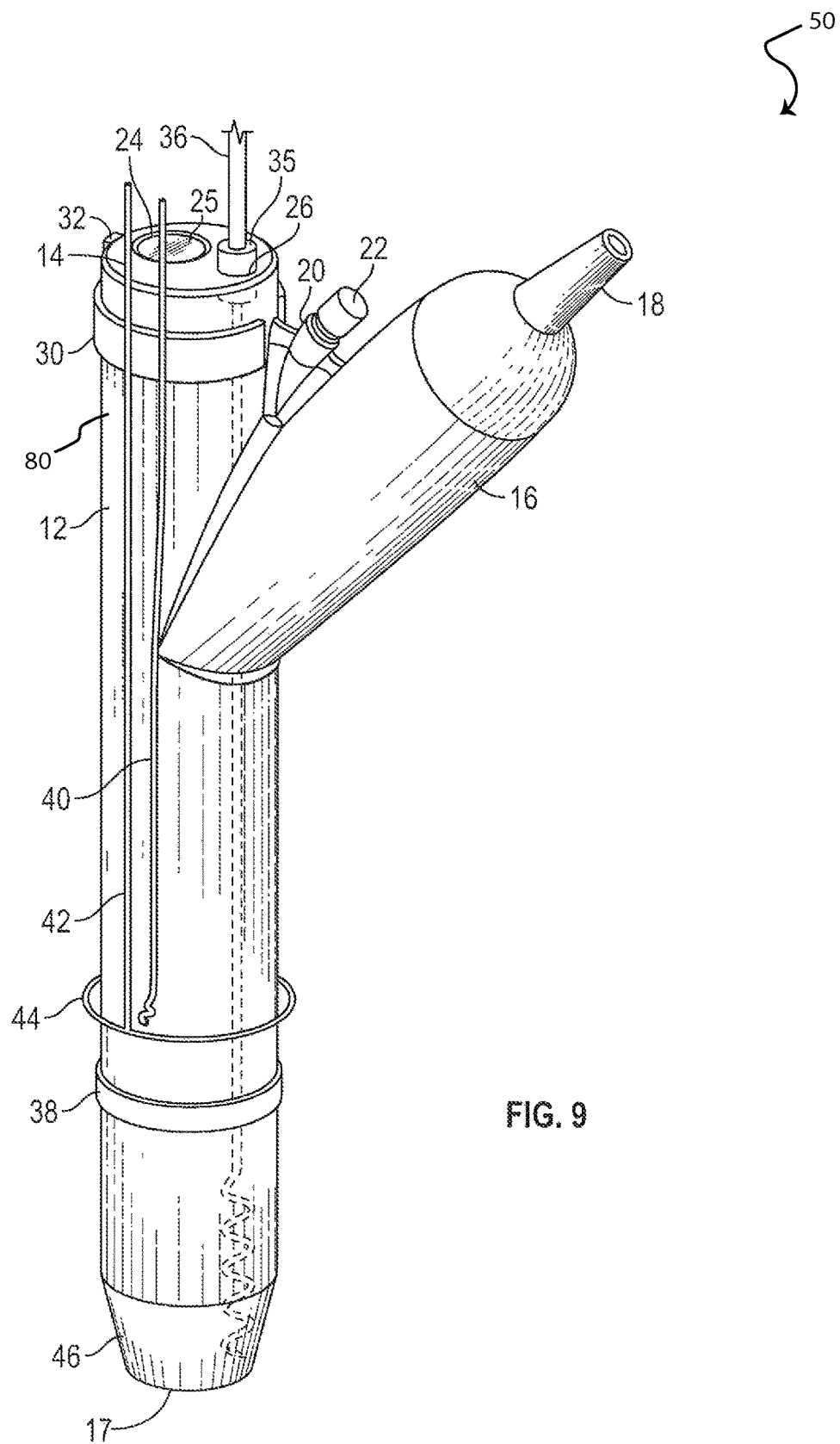
FIG. 9 is a view of an anatomic structure extractor with both a cutting wire and a ligature deployer.

In some embodiments, cap 14 further comprises a needle port 26. Needle port 26, as shown in FIG. 1 and FIGS. 3-9, is an opening in cap 14 through which a medial practitioner may insert a long needle, for example a needle 36 as shown by FIG. 4 and FIG. 9, to aspirate fluid or semi-fluid contents from a cyst or mass located at open end 17 (See FIG. 2) of tubular member 12. In some embodiments, needle 36 is used by the medical practitioner to obtain a core biopsy, an aspiration biopsy, or the like wherein the anatomical structure of interest is a solid mass, nodule, tumor, or other solid tissue structure amenable to needle aspiration biopsy for cytology, and/or needle-core tissue biopsy.

In some embodiments, needle port 26 further comprises a seal 35 (not shown in FIG. 1; see FIG. 4 and FIG. 9). Seal 35 may be formed from any material which is sufficient resilient or elastic to press around a needle, such as needle 36, and allow smooth movement of the needle to-and-fro as needed through needle port 26. Non-limiting examples of such material include rubber, silicone, combination materials such as Silastic™, and the like.

Needle 36 may be passed through seal 35 into a lumen of tubular member 12 to contact an anatomical structure of interests at open end 17. Accordingly, needle 36 is sufficiently longer than a coupled structure of tubular member 12 and cap 14. Needle 36 is used by the medical practitioner to puncture an anatomical structure of interest, such as a cyst or mass lesion for example. Needle 36, in some embodiments, is a straight needle, a "corkscrew" needle, or the like. In some embodiments, needle 26 comprises a central bore through which a solid, sharp-tipped stylus is inserted to facilitate entry into the anatomical structure of interest by puncturing the wall of the structure. Following entry into the structure, the stylus is removed to allow evacuation of material from the structure. Additionally, material, such as air, saline, or other fluid may be injected into the structure to facilitate the evacuation of viscous or semi-solid content, such as mucous, coagulated blood, sebaceous material, and the like. In some embodiments wherein needle 36 is an corkscrew-shaped needle, needle 36 may be used by a medical practitioner to bore through solid or semisolid material and to anchor needle 36 to a cyst wall, a mass, the tissue of a hollow organ, or the like while material within the lumen of said cyst, mass, etc. is aspirated or collected for examination. Wherein needle 36 is a corkscrew needle, a medical practitioner may anchor needle 36 into the cyst wall, mass, etc. and mechanically retract the structure into anatomic structure extractor 10 through open end 17 of tubular member 12.

Wherein the probe is a tissue morcellizing auger 37, extraction of denser tissue from within the anatomical structure is facilitated. For example, wherein the anatomic structure is a dermoid lesion, hair, cartilage, and the like which may be present within the anatomic structure can be morcellized and subsequently extracted. The morcellized tissue is evacuated into a trap 16 by applying suction to vacuum port 18 simultaneously as the material is morcellized, wherein the morcellized material is immediately evacuated into trap 15 preventing contamination of the surrounding tissue or embolization of material into the patient's venous circulation. In some embodiments, tissue morcellizing auger 37 comprises a motor electrically coupled to a power source, wherein the motor causes a cutting end 29 of tissue morcellizing auger 37 to rotate.

In some embodiments, any of a variety of probes, some of which are placed prior to the insertion of anatomic structure extractor 10 into the patient.

Open end 17 opposite proximal end 80 of tubular member 12 is open to allow anatomic structure extractor 10 to form a seal or partial seal against the surface of an anatomical structure of interest. Such seal or partial seal prevents or limits contamination of surrounding structures by potentially infected or neoplastic contents of the anatomical structure of interest while performing aspiration of other procedure on the structure. Accordingly, it is desirable for essentially the entire perimeter of open end 17 to contact the anatomical structure of interest. This is particularly important during use of anatomic structure extractor 10 to aspirate an appendiceal or periappendiceal abscess, an abscessed or necrotic gallbladder, or other intra-abdominal/retroperitoneal abscess.

In some embodiments, open end 17 of tubular member 12 forms an angle "B," as shown in FIG. 4. Angle B facilitates insertion of open end 17 of tubular member 12 through an incision in the abdominal or chest wall of a patient. In some embodiments, Angle B is about 30 degrees. In some embodiments, Angle B is about 45 degrees. In some embodiments, Angle B is in a range of from about fifteen (15) degrees to about fifty (50) degrees. A lip 34, as shown in FIGS. 1-4 and FIG. 7, is coupled to open end 17 and facilitates both 1) insertion of open end 17 through an incision; and 2) sealing of open end 17 against an anatomical structure of interest. Lip 34, in some embodiments, is a flared ring of the material forming tubular member 12 at open end 17. Alternatively, lip 34 may be formed from any material, such as Silastic™, for example, that aids in sealing open end 17 of tubular member 12 to the surface of an anatomical structure of interest and which helps to prevent leakage of any contents of the structure into the anatomical space adjacent to the structure.

Figure 3:
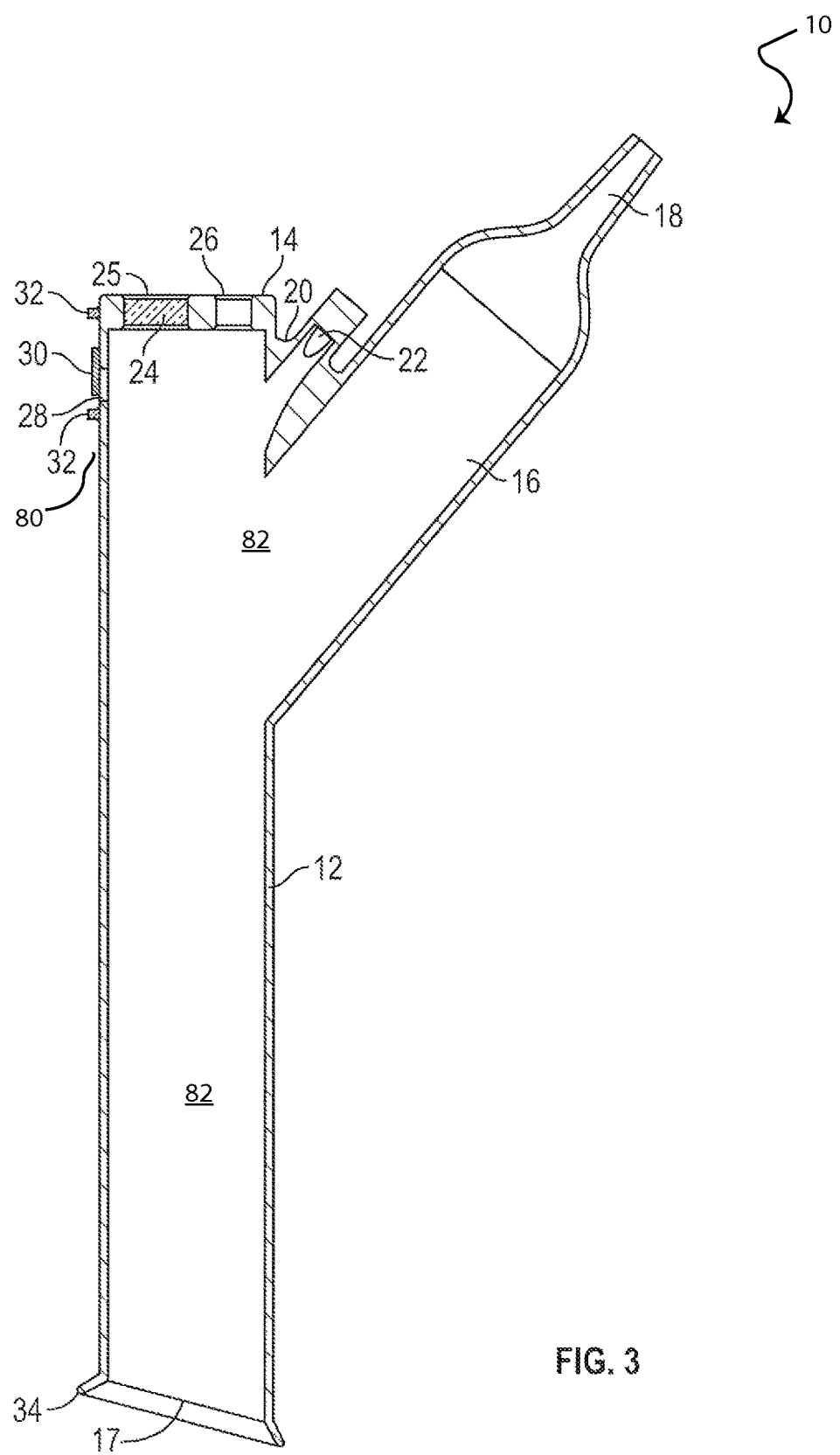
FIG. 3 is a cross sectional view of an anatomic structure extractor.
Figure 4:
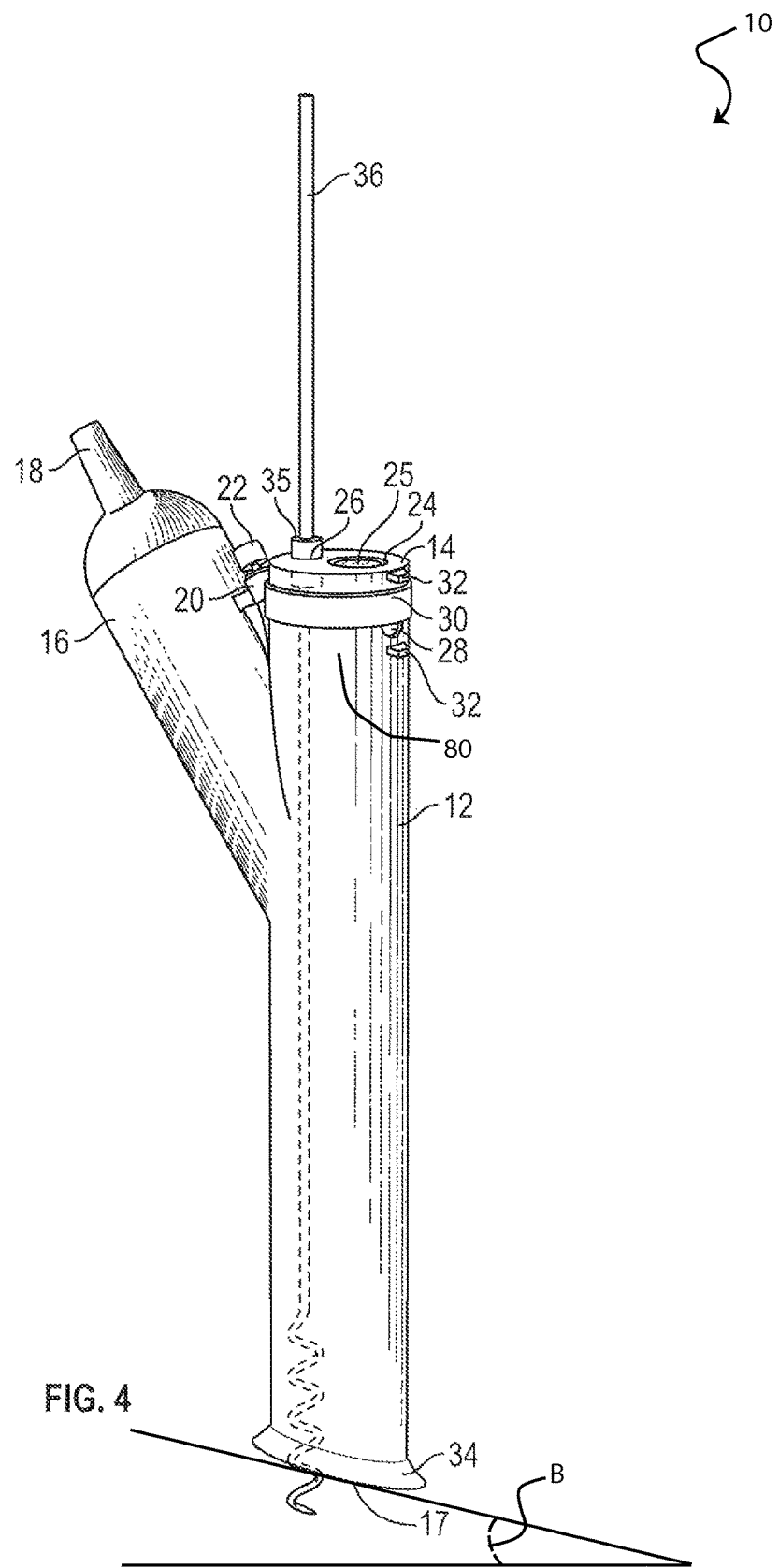
FIG. 4 is an isometric view of an anatomic structure extractor with a corkscrew needle.

As shown in FIGS. 1-6, a trap 16 is coupled to tubular member 12 and is in fluid communication with tubular member 12. Trap 16 acts to catch any fluid, tissue, gel, or other material removed from the anatomical structure of interest. Trap 16 also holds said material in a location within anatomic structure extractor 10 where the medical practitioner's view of the anatomical structure of interest is not impeded. Trap 16, as shown in FIG. 3, is an open chamber that branches off at an angle from the main tubular member 12. Trap 16 may be any desired size or shape, so long as trap 16 has adequate capacity to hold sufficient material. In some embodiments, trap 16 is translucent or transparent, similar to tubular member 12 as discussed herein above.

Trap 16 is in fluid communication with tubular member 12 on one end and in fluid communication with a suction post 18 at an opposite end. Suction post 18, in some embodiments, is designed to have a vacuum source coupled to a top end. Suction post 18 is a smaller tubular member that narrows towards a top end, as shown in FIG. 3. A bottom of suction post 18 is coupled to trap 16. Suction post 18 may, however, be formed in any shape desired so long as the shape allows a vacuum source to be coupled to trap 16. Suction post 18 may be in fluid communication with trap 16 or may be limited to vacuum communication with trap 16. In embodiments wherein suction post 18 is merely in vacuum communication with trap 16, a barrier may be placed, in some embodiments, between suction post 18 and trap 16 to allow transmission of a vacuum negative pressure to trap 16, but would prevent any solid, semi-solid, or liquid material from passing from trap 16 into suction post 18, thus preventing passage of such solid, semi-solid, or liquid material from anatomic structure extractor 10 into a vacuum source.

In some embodiments, an external vacuum source applied suction anatomic structure extractor 10. Suction draws material removed from the anatomical structure of interest into trap 16. The suction also provides an adequate vacuum to pull the surface of the anatomical structure of interest into anatomic structure extractor 10. Suction may also be applied to suction post 18 by a suction bulb or any device or method which produces a desired vacuum within anatomic structure extractor 10.

Figure 5:
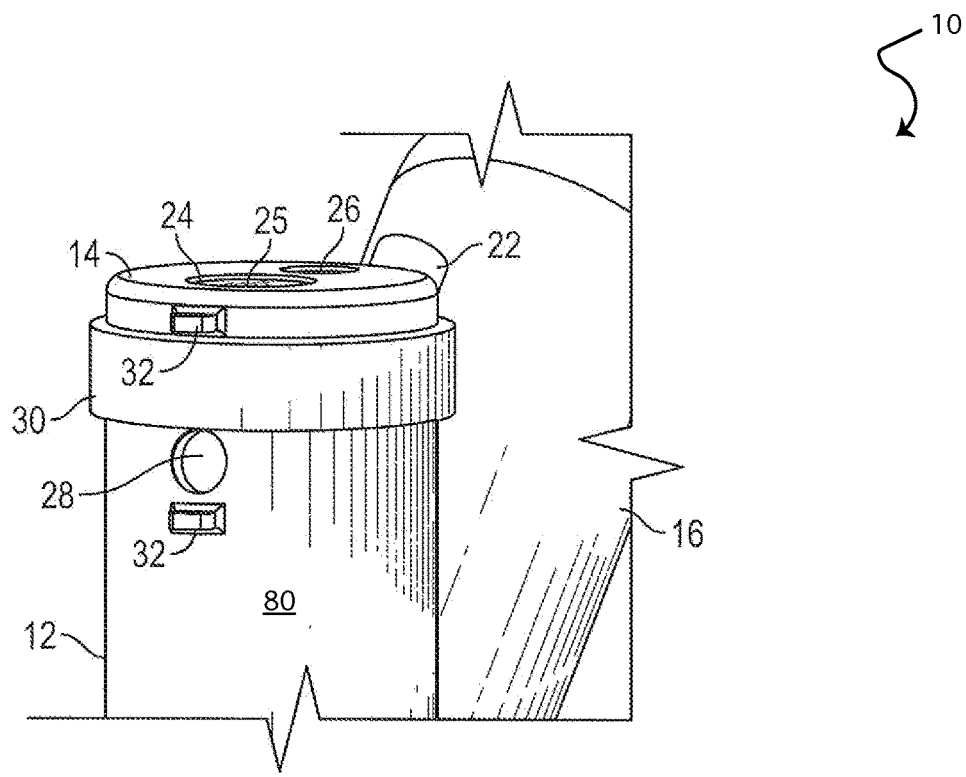
FIG. 5 is a view of an open vacuum break on an anatomic structure extractor.
Figure 6:
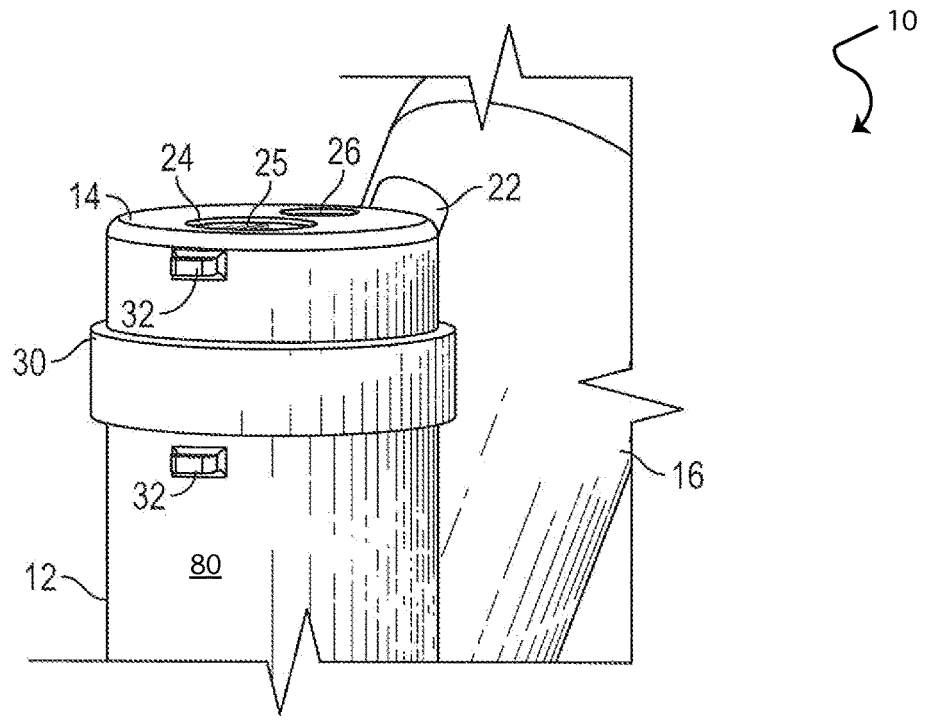
FIG. 6 is a view of a closed vacuum break on an anatomic structure extractor.

The suction force within anatomic structure extractor 10 created by the external vacuum source is regulated, in some embodiments by a vacuum break 28, as shown in FIG. 5 and FIG. 6. Vacuum break 28 is an opening proximate to proximal end 80 of tubular member 12, in some embodiments. Conceivably, vacuum break 28 may be located elsewhere along tubular member 12 or on anatomic structure extractor 10 wherein suction is applied. In the figures, vacuum break 28 is shown as a generally round hole in tubular member 12, however this is not meant to be limiting. Vacuum break 28, in some embodiments, may be of any shape desired.

In some embodiments, vacuum break 28 is covered by a vacuum break cover 30, which is generally a ring which surrounds the circumference of tubular member 12 and engages tubular member 12 to move along a continuum between a fully raised "open" position and a fully lowered "closed" position. When in the fully raised open position, vacuum break 28 freely transmits suction at or near the set negative pressure of the external vacuum source coupled to suction post 18 to the interior of anatomic structure extractor 10. Also, when an external vacuum source is not coupled to anatomic structure extractor 10 and suction post 18 is open to ambient pressure, the pressure within anatomic structure extractor 10 equilibrates with the ambient pressure and no vacuum exists within tubular member 12. Conversely, when in the lowered position, vacuum break cover 30 closes and seals vacuum break 28 so that any negative pressure existing within anatomic structure extractor 10 at the time vacuum break 28 is closed is preserved, so long as an airtight seal of open end 17 against the surface of an anatomical structure of interest exists. Under a condition wherein an external vacuum source is coupled to suction post 18 of anatomic structure extractor 10 and vacuum break 28 is in a position along the continuum between the fully raised open position and the fully lowered closed position, the degree of negative pressure within anatomic structure extractor 10 is at a value between the set negative pressure of the external vacuum source and ambient pressure. Therefore a medical practitioner using anatomic structure extractor 10 may vary the amount of negative pressure within anatomic structure extractor 10 by adjusting the position of vacuum break 28 along the continuum between the fully raised open position and the fully lowered closed position.

Vacuum break cover 20, though illustrated as a ring, can be any shape or form that can be used to cover the vacuum break 28. For example, vacuum break cover 30, in some embodiments, is the thumb of the medical practitioner. In some such embodiments, the medical practitioner's thumb is placed partially or completely over vacuum break 28 to partially or completely cover it, wherein the medical practitioner can regulate the degree of negative pressure from an external vacuum source transmitted to the interior of anatomic structure extractor 10. In some embodiments, vacuum break cover 30 is a plate formed of suitable material that slides in a channel coupled to tubular member 12, wherein vacuum break 28 is located within the channel and vacuum break cover 30 is slidably coupled to the channel to move partially or completely over vacuum break 28 and creating a substantially airtight seal with seal vacuum break 28, to the extent that vacuum break cover 30 partially or completely covers vacuum break 28.

A cover stop 32 prevents vacuum break cover 30 from inadvertently uncoupling from anatomic structure extractor 10. Cover stop 32, in some embodiments, is two cover stops 32—one stop 32 above (proximal) the vacuum break cover 30 and a second stop 32 below (distal) vacuum break cover 30.

Cover stop 32, as illustrated in the drawing figures, is a raised area on an outer surface of tubular member 12 of anatomic structure extractor 10. These raised areas are small, slightly rectangular areas in the drawing figures, however, they may be any type of raised area which prevents or resists vacuum break cover 30 from sliding off anatomic structure extractor 10. Cover stop 32, in some embodiments, is a circular, raised area; a square, raised area; a pyramidal, raised area; or the like. Cover stop 32, in some embodiments, is formed as a unitary body with a component of anatomic structure extractor 10, such as at proximal end 80 of tubular member 12, for example.

A light post 20, in some embodiments, is coupled to tubular member 12. Light post 20 is a solid, translucent or transparent cylindrical member located at proximal end 80 of tubular member 12 in a space extending from tubular member 12 to trap 16, as shown in FIG. 7. Light post 20, in some embodiments, is any size or shape desired so long as light post 20 is able to couple to light source 22 and allow light to be transmitted through lumen 82 of tubular member 12.

In some embodiments, light source 22 is a surgical light source transmitted through a fiber optic cable coupling to light post 20. Such surgical light sources are commercially available and widely known to those in the art of light sources for coupling to medical devices.

FIGS. 7-10 show some alternative embodiments of an anatomic structure extractor. An anatomic structure extractor 50, as shown in FIGS. 7-10, may be used for performing drainage, extraction, or other surgical procedures upon a solid organ, or a tubular organ such as a gallbladder of an appendix, for example. Some embodiments of anatomic structure extractor 50 comprise additional elements, as distinguished from anatomic structure extractor 10, which aid in the amputation and resection of structures. Other than the additional elements and variations of embodiments discussed herein below, anatomic structure extractor 50 comprises the same elements as embodiments of anatomic structure extractor 10.

FIG. 7 shows anatomic structure extractor 50, including a cutting wire 44 and a wire handle 42. Cutting (amputating) wire 44, in some embodiments, is a ring of thin, small-gauge wire that is used to "snare" and amputate tissue. Cutting wire 44 surrounds tubular member 12 of anatomic structure extractor 50. Cutting wire 44, in some embodiments, is an electrode through which a medical practitioner may apply current from an external source coupled to wire handle 42, to cauterize the tissue being amputated. Cutting wire 44, in some embodiments, is configured into a generally circular shape, as shown in FIGS. 7-9. In some embodiments, cutting wire 44 is a small loop, arch, or the like. Cutting wire 44 may be formed in any shape desired, provided cutting wire 44 is able to amputate the target tissue from its stump, vascular pedicle, base, or other attachment.

Cutting wire 44 is coupled to wire handle 42. Wire handle 42 allows a medical practitioner to manipulate cutting wire 44 from proximal end 80 of tubular member 12. Wire handle 42, in some embodiments, is any shape or length, and formed from any material desired to serve the intended purpose. In some embodiments, wire handle 42 is coupled to anatomic structure extractor 50. In some embodiments, wire handle 42 is reversibly coupled to anatomic structure extractor 50, such that a medical practitioner may select from a plurality of shapes, sizes, and configurations of wire handle 42 and cutting wire 44 desired to serve the intended purpose.

FIG. 8 shows anatomic structure extractor 50 further comprising a constricting ligature 38 and a ligature deployer 40. Constricting ligature 38, in some embodiments, is an elastomeric ring and is used to compress tissue drawn into constricting ligature 30, thereby preventing blood flow to the tissue and allowing amputation and resection of tissue distal to constricting ligature 38. Constricting ligature 38, in some embodiments, is used to stop blood flow between an organ, such as the appendix, and the vascular pedicle of the organ. Following placement of constricting ligature 38 around a base or vascular pedicle of a tissue or organ, the tissue or organ may be resected without significant blood loss.

Constricting ligature 38, in some embodiments, is positioned around tubular member 12 of anatomic structure extractor 50. In such embodiments, open end 17 of tubular member 12 comprises a taper 26, as shown in FIG. 8. Taper 46, in some embodiments, is a narrowing of the diameter of tubular member 12 and allows a medical practitioner to slide constricting ligature 38 off of tubular member 12 on to a base/vascular pedicle of a tissue or organ the medical practitioner has drawn into open end 17 of tubular member 12.

A medical practitioner pushes constricting ligature 38 off of tubular member 12 across taper 46 with a ligature deployer 40, as shown in FIG. 9. Ligature deployer 40, in some embodiments, is a rigid wire with a handle which pushes constricting ligature 38 forward in response to a force applied to the end of ligature deployer 40 nearest proximal end 80 of tubular member 12 by a medial practitioner seeking to deploy constricting ligature onto a pedicle of tissue, such as a vascular pedicle, drawn in to open end 17 of tubular member 12. In some embodiments, ligature deployer 40 is any device formed to allow a medical practitioner to cause constricting ligature 38 to pass from tubular member 12 onto the base of a tissue or vascular pedicle. In some embodiments, ligature deployer 40 is coupled to anatomic structure extractor 50. In some embodiments, ligature deployer 40 is not coupled to anatomic structure extractor 50.

Figure 10:
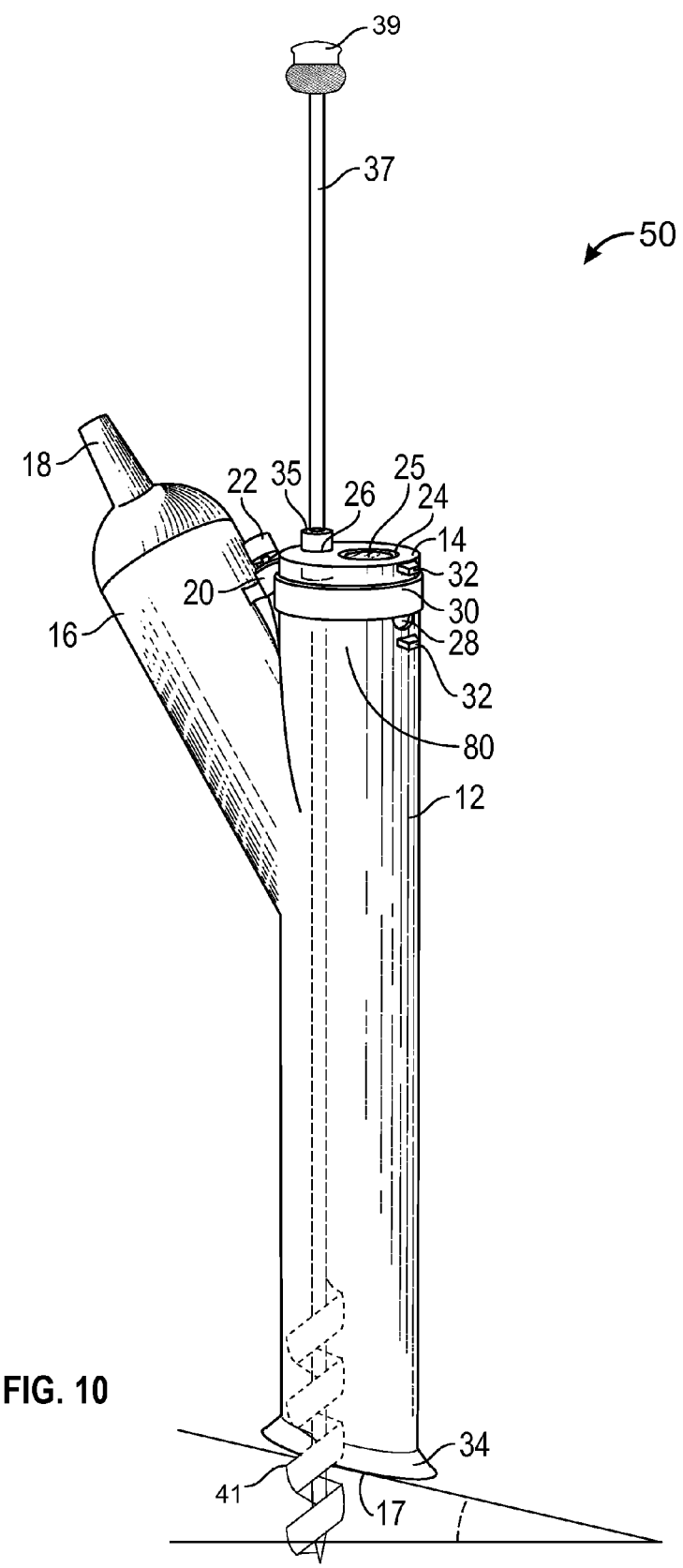
FIG. 10 is a perspective view of a tissue morcellizing auger coupled to a needle port of an anatomic structure extractor.

FIG. 10 shows anatomic structure extractor 50 fitted with morcellizing auger 37. In some embodiments, morcellizing auger 37 couples to needle port 35 wherein a surgeon can slide morcellizing auger 37 in-and-out of needle port 35. In the embodiment shown in FIG. 10, morcellizing auger 37 is hand-turned by a surgeon grasping knob 39. In some embodiments, a motor (not shown) couples to morcellizing auger 37, turning morcellizing auger 37. A surgeon inserts a cutting blade 41 into the anatomic structure wherein by rotating morcellizing auger 37, cutting blade 41 morcellates dense material or tissue within the anatomic structure. Wherein the surgeon maintains contact of lip 35 with a surface of the anatomic structure, morcellized contents of the structure may be drawn by vacuum suction into trap 16.

Some embodiments of anatomic structure extractor 50 do not comprise needle port 26. In some embodiments, anatomic structure extractor 10 and/or anatomic structure extractor 50 are used as a specimen container for processing fluid or tissue removed from a patient and contained within lumen 82 of tubular member 12 or (specimen) trap 16. In such embodiments, this function obviates additional handling of infected or contaminated fluids and tissues by medical practitioners and other health care personnel, such as operating room personnel, for example. In such embodiments, a cover is used to seal open end 17, suction post 18, and any additional opening which communicates with lumen 82 of tubular member 12 and/or trap 16 and prevents leakage or spillage of fluids or specimens contained therein.

Accordingly, for the exemplary purposes of this disclosure, the components defining any embodiment of the invention may be formed as a single unitary body if it is possible for a component of the invention to serve its intended function. Components may be created or manufactured from many different types of materials or combinations thereof that can be readily be formed into shaped objects, provided that the materials selected are consistent with the intended mechanical operation of the invention. For example, the components may be formed of natural or synthetic rubbers; glasses; composites such as fiberglass, carbon-fiber, and/or other similar materials; polymers such as plastic, polycarbonate, polyvinylchloride plastic, ABS plastic, polystyrene, polypropylene, acrylic, nylon, and phenolic plastic or any combination thereof and/or other like materials; metals such as zinc, magnesium, titanium, copper, iron, steel, stainless steel, any combination thereof, and/or other like materials; alloys such as aluminum and/or other like materials, any other suitable material, and/or any combination thereof.

Figure 11:
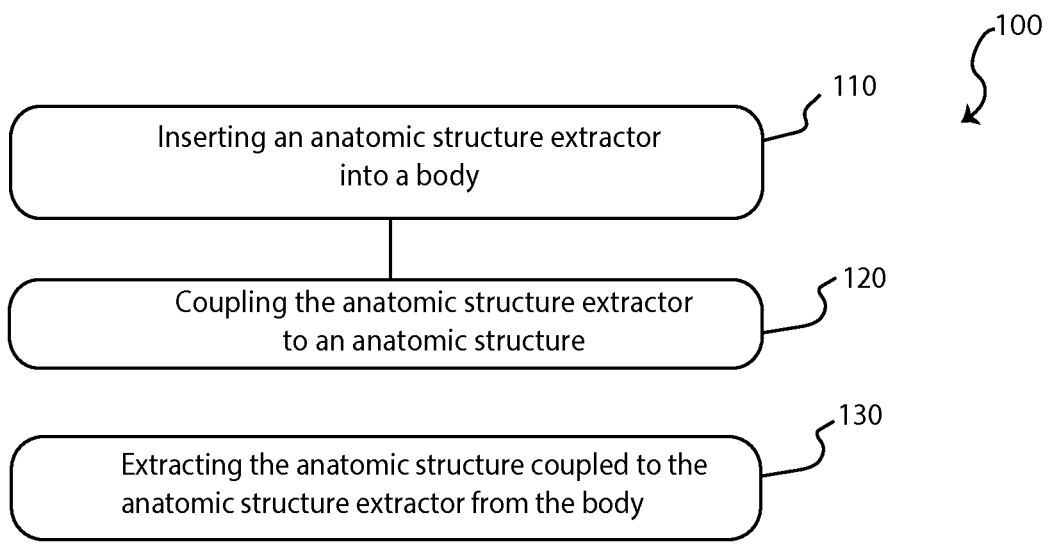
FIG. 11 is a flow chart of a method of using an anatomic structure extractor.

FIG. 11 is a schematic flow-chart representation of a method 100 of using an anatomic structure extractor. Method 100 comprises an inserting step 110, a coupling step 120, and an extracting step 130. It is anticipated that all steps of method 100, in some embodiments, are performed by a medical practitioner.

Inserting step 110 comprises inserting an anatomic structure extractor into a body. Inserting step 110 may be performed transcutaneously by making a skin incision into a body and inserting the anatomic structure extractor into the body through the skin incision; alternatively, inserting step 110 may be performed by inserting the anatomic structure extractor through a mucosal incision. In some embodiments, an incision in the skin or mucosa is not necessary and the anatomic structure extractor is passed trans-vaginally, trans-rectally, or orally into the body.

Coupling step 120 comprises coupling the anatomic structure extractor to an anatomic structure. In some embodiments, coupling step is accomplished by contacting a lip of the anatomic structure extractor to an anatomic structure and applying suction to a suction post on the anatomic structure extractor. In some embodiments, coupling step 120 comprises inserting a corkscrew needle through a needle port on the anatomic structure extractor and screwing the corkscrew needle into the anatomic structure. In some embodiments, coupling step 120 comprises boring a morcellizing auger coupled to the anatomic structure extractor into the anatomic structure.

Extracting step 130 comprises extracting the anatomic structure coupled to the anatomic structure extractor from the body.

This invention overcomes the aforementioned and other difficulties encountered with using prior art, like the need for multiple puncture incisions of the abdominal or chest wall and the need for general or spinal anesthesia to allow retraction of the abdominal wall. Exceptional results can be obtained with the anatomic structure extractor and methods of use, as described herein disclosing several embodiments of the invention. The anatomic structure extractor is inexpensive to manufacture and easy to use. Thus, the disclosed method of use and various embodiments of the anatomic structure extractor device have immediate applicability in the delivery of patient care throughout the healthcare industry.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

What is claimed is:

1. A method of removing an anatomic structure from a patient comprising the steps of:
    inserting into a patient an anatomic structure extractor comprising a tubular member and a handle in fluid communication with the tubular member;
    coupling the anatomic structure extractor to an anatomic structure; and
    extracting the anatomic structure coupled to the anatomic structure extractor from the patient, wherein said anatomic structure extractor further comprises
    a cap coupled to an end of said tubular member wherein said cap further comprises at least one view port and at least one needle port;
    a trap in fluid communication with said tubular member, wherein the diameter of the tubular member is substantially equal to the diameter of the trap;
    a suction post in communication with said trap; and
    a light post coupled to said tubular member.

2. The method of claim 1, wherein the anatomic structure is a non-fluid-filled structure.

3. The method of claim 1, wherein the anatomic structure is a solid structure.

4. The method of claim 1, wherein the inserting step comprises a trans-vaginal insertion.

5. The method of claim 1, wherein the inserting step comprises a trans-cutaneous insertion.

6. The method of claim 1, wherein the inserting step comprises a trans-mucosal insertion.

7. The method of claim 1, wherein the coupling step comprises applying a vacuum to a suction post of the anatomic structure extractor.

8. The method of claim 1, wherein the coupling step comprises boring a corkscrew needle inserted through a needle port in the anatomic structure extractor into the anatomic structure.

9. A method for removing an anatomic structure from a patient comprising the steps of:
    inserting an anatomic structure extractor into a patient;
    coupling the anatomic structure extractor to an anatomic structure;
    boring a morcellizing auger coupled to the anatomic structure extractor into the anatomic structure;
    removing a material from the anatomic structure with the morcellizing auger; and
    extracting the material from the patient, wherein said anatomic structure extractor comprises
    a tubular member;
    a cap coupled to an end of said tubular member wherein said cap further comprises at least one view port and at least one needle port;
    a trap in fluid communication with said tubular member, wherein the diameter of the tubular member is substantially equal to the diameter of the trap;
    a suction post in communication with said trap; and
    a light post coupled to said tubular member.

10. The method of claim 9, further comprising a suctioning step, wherein the suctioning step comprises applying a vacuum to the suction post of the anatomic structure extractor.

11. A method for removing an anatomic structure from a patient comprising the steps of:
    coupling an anatomic structure extractor to an anatomic structure in a patient;
    controlling a vascular pedicle of the anatomic structure;
    applying suction to the anatomic structure extractor;
    retracting said anatomic structure into the anatomic structure extractor; and
    removing the anatomic structure from the patient, wherein said anatomic structure extractor comprises
    a tubular member;
    a cap coupled to an end of said tubular member wherein said cap further comprises at least one view port and at least one needle port;
    a trap in fluid communication with said tubular member, wherein the diameter of the tubular member is substantially equal to the diameter of the trap;
    a suction post in communication with said trap; and
    a light post coupled to said tubular member.

12. The method of claim 11, wherein the controlling step comprises ligating said vascular pedicle.

13. The method of claim 12, wherein the controlling step further comprises pushing a ligating band onto said vascular pedicle.

14. The method of claim 11, wherein the anatomic structure is an organ.

15. The method of claim 14, wherein the organ is an appendix.

16. The method of claim 11, wherein said anatomic structure extractor further comprises a vacuum break in fluid communication with said suction post.

17. The method of claim 11, wherein said anatomic structure extractor further comprises a corkscrew needle inserted through said at least one needle port.

18. The method of claim 11, wherein said anatomic structure extractor further comprises a morcellizing auger inserted through said at least one needle port.

19. The method of claim 11, wherein said at least one view port further comprises a magnifying lens.

* * * * *